US008617216B2

(12) United States Patent
Brumfield

(10) Patent No.: US 8,617,216 B2
(45) Date of Patent: Dec. 31, 2013

(54) FULLY-ADJUSTABLE BONE FIXATION DEVICE

(75) Inventor: David L. Brumfield, Collierville, TN (US)

(73) Assignee: David L. Brumfield, Collierville, TN (US)

( * ) Notice: Subject to any disclaimer, the term of this patent is extended or adjusted under 35 U.S.C. 154(b) by 25 days.

(21) Appl. No.: 12/931,371

(22) Filed: Feb. 1, 2011

(65) Prior Publication Data
US 2011/0245876 A1 Oct. 6, 2011

Related U.S. Application Data

(60) Provisional application No. 61/341,762, filed on Apr. 5, 2010.

(51) Int. Cl.
*A61B 17/70* (2006.01)
(52) U.S. Cl.
USPC ............................... 606/266; 606/246
(58) Field of Classification Search
USPC ................... 606/78, 301–321, 911
See application file for complete search history.

(56) References Cited

U.S. PATENT DOCUMENTS

| | | | |
|---|---|---|---|
| 4,854,311 A | 8/1989 | Steffee | |
| 5,474,555 A | 12/1995 | Puno et al. | |
| 5,501,684 A * | 3/1996 | Schlapfer et al. | 606/301 |
| 5,728,098 A | 3/1998 | Sherman et al. | |
| 5,733,285 A * | 3/1998 | Errico et al. | 606/278 |
| 5,879,350 A | 3/1999 | Sherman et al. | |
| 5,885,285 A | 3/1999 | Simonson | |
| 5,947,967 A | 9/1999 | Barker | |
| 5,954,725 A | 9/1999 | Sherman et al. | |
| 5,984,924 A | 11/1999 | Asher et al. | |
| 6,050,997 A | 4/2000 | Mullane | |
| 6,132,434 A | 10/2000 | Sherman et al. | |
| 6,183,473 B1 | 2/2001 | Ashman | |
| 6,210,413 B1 | 4/2001 | Justis et al. | |
| 6,254,602 B1 | 7/2001 | Justis | |
| 6,273,888 B1 | 8/2001 | Justis | |
| 6,280,442 B1 | 8/2001 | Barker et al. | |
| 6,287,311 B1 | 9/2001 | Sherman et al. | |
| 6,371,957 B1 | 4/2002 | Amrein et al. | |
| 6,375,657 B1 * | 4/2002 | Doubler et al. | 606/309 |
| 6,379,357 B1 | 4/2002 | Bernstein et al. | |
| 6,402,749 B1 | 6/2002 | Ashman | |
| 6,562,038 B1 | 5/2003 | Morrison | |
| 6,626,906 B1 | 9/2003 | Young | |
| 6,685,705 B1 | 2/2004 | Taylor | |
| 6,887,242 B2 | 5/2005 | Doubler et al. | |
| 7,022,122 B2 | 4/2006 | Amrein et al. | |
| 7,195,633 B2 * | 3/2007 | Medoff et al. | 606/309 |

(Continued)

*Primary Examiner* — Jerry Cumberledge
(74) *Attorney, Agent, or Firm* — Haynes and Boone, LLP

(57) ABSTRACT

An orthopedic stabilization system of implants that includes a bone attachment means that provides poly-axial fixation of the system to the vertebrae, and a connector means that connects the bone attachment means to the spinal rod in a fashion that allows variable height adjustment of the spinal rod (dorsal in the case of posterior spinal pedicle fixation). The orthopedic stabilization system includes a locking means with a tightenable ball-joint arrangement that locks a post means to the bone attachment means in a desired relative spatial orientation. Several embodiments are disclosed, some using traditional mechanical locking means such as screw fasteners, taper-locking interfaces and collets. Embodiments are described that use the austenitic transformation of shape memory alloy (SMA) material to effect a locking of both the ball-joint arrangement and the connector means.

7 Claims, 10 Drawing Sheets

(56) References Cited

U.S. PATENT DOCUMENTS

| | | |
|---|---|---|
| 7,585,299 B2 | 9/2009 | Rezach |
| 7,678,136 B2 | 3/2010 | Doubler et al. |
| 7,763,057 B2 * | 7/2010 | Abdelgany et al. ............ 606/305 |
| 7,892,257 B2 * | 2/2011 | Abdelgany .................... 606/246 |
| 2002/0032443 A1 | 3/2002 | Sherman et al. |
| 2003/0023240 A1 | 1/2003 | Amrein et al. |
| 2005/0070901 A1 | 3/2005 | David |
| 2005/0131404 A1 | 6/2005 | Mazda et al. |
| 2005/0192571 A1 * | 9/2005 | Abdelgany ..................... 606/61 |
| 2005/0192572 A1 * | 9/2005 | Abdelgany et al. ............. 606/61 |
| 2005/0277924 A1 * | 12/2005 | Roychowdhury ............... 606/61 |
| 2006/0036252 A1 * | 2/2006 | Baynham et al. ............... 606/73 |
| 2008/0119858 A1 | 5/2008 | Potash |
| 2008/0262545 A1 | 10/2008 | Simonson |
| 2008/0306551 A1 * | 12/2008 | Sanders et al. ................ 606/301 |
| 2009/0143827 A1 | 6/2009 | Levy et al. |
| 2009/0326587 A1 * | 12/2009 | Matthis et al. ................ 606/264 |
| 2010/0036436 A1 * | 2/2010 | Winslow et al. ............... 606/305 |
| 2010/0049253 A1 | 2/2010 | Miller |

\* cited by examiner

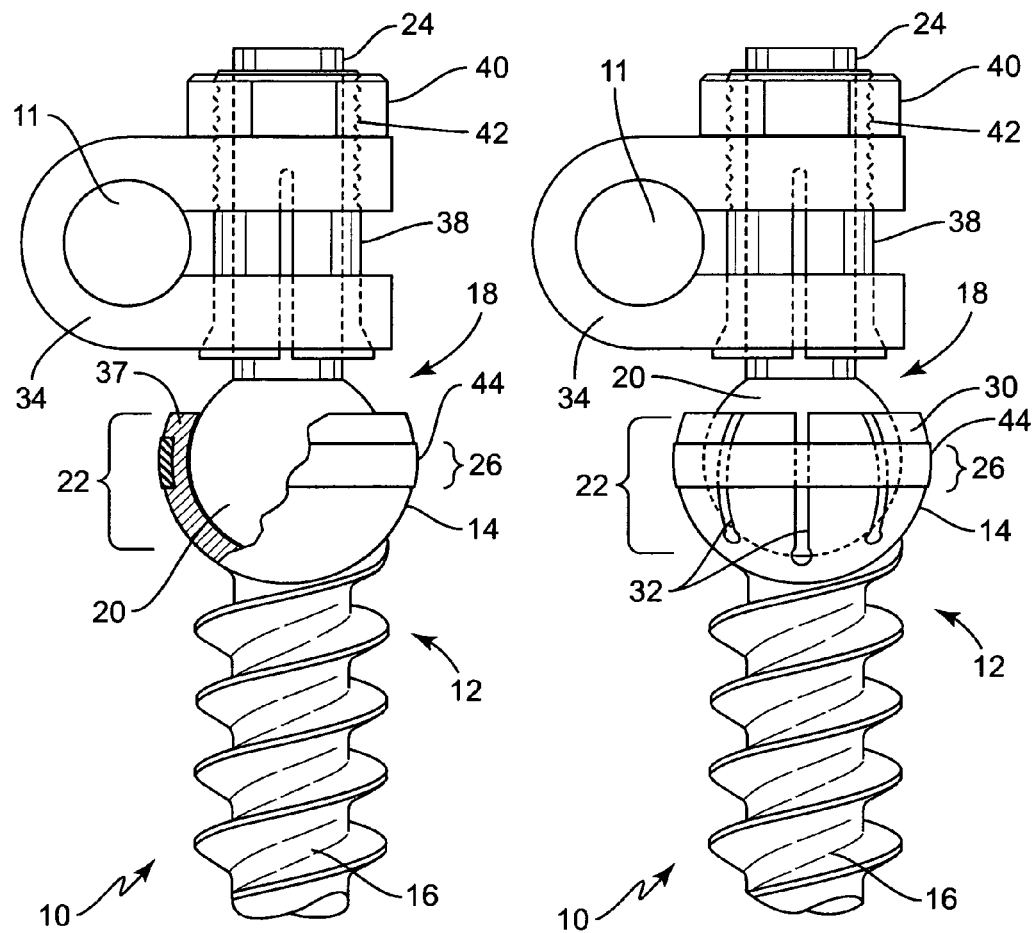
*FIG. 3A*  *FIG. 3B*

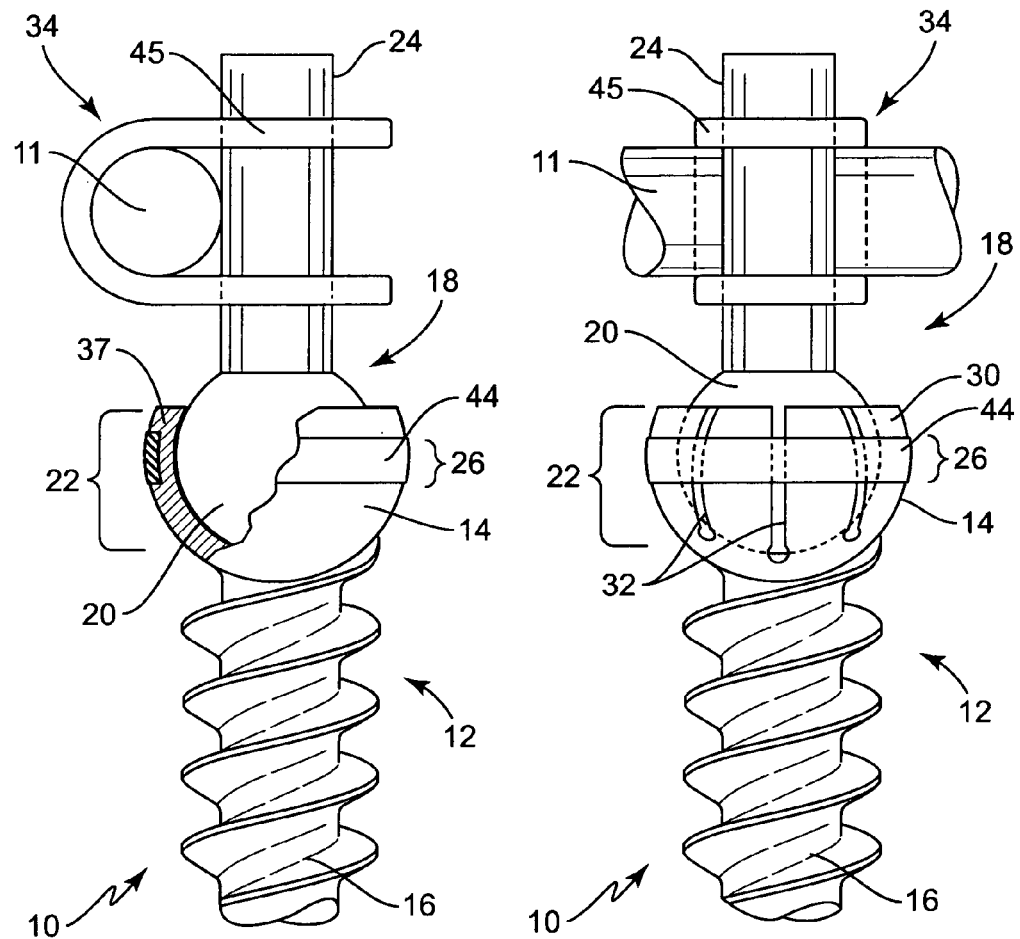
*FIG. 4A*      *FIG. 4B*

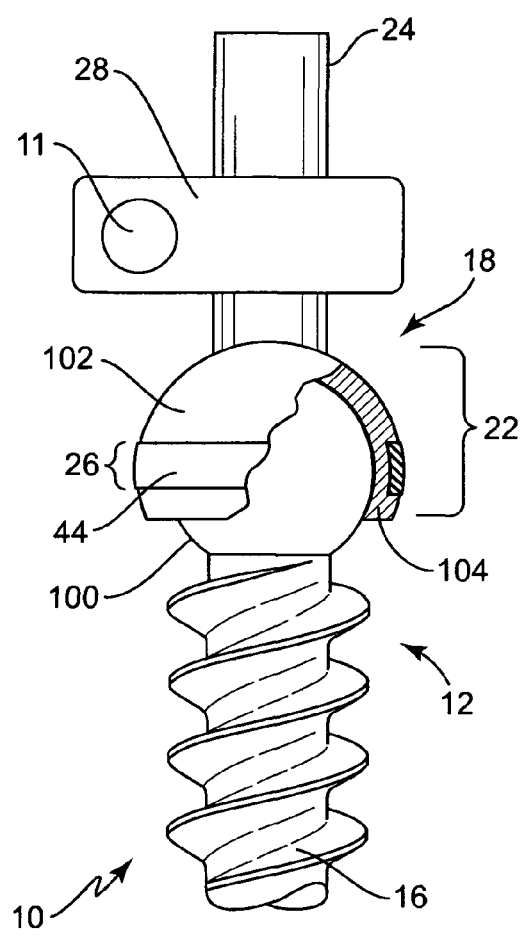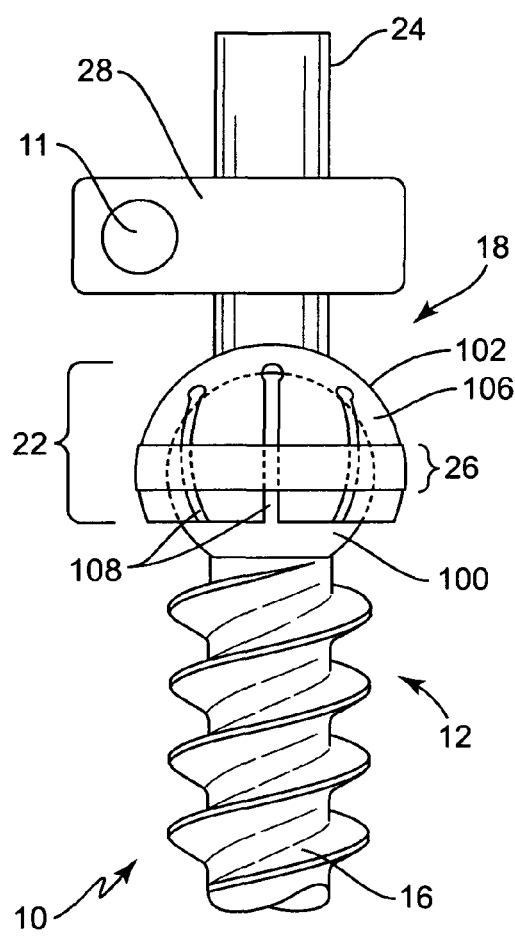
FIG. 6A  FIG. 6B

FULLY-ADJUSTABLE BONE FIXATION DEVICE

CROSS-REFERENCE TO RELATED APPLICATIONS

This application claims the benefit of U.S. Provisional Application No. 61/341,762, filed Apr. 5, 2010.

TECHNICAL FIELD

The field to which the disclosure generally relates includes orthopedic stabilization and spinal fixation of vertebrae, and in particular, a bone stabilization system that allows between the bone attachment means, e.g. screw, and longitudinal member, e.g. rod, all of the features of poly-axial positioning, variable height (dorsal) positioning, and a bulbous bone-metal interface for low-profile, stronger fixation to bone without restricting positioning.

BACKGROUND

Spinal implant systems can be engaged to or along one or more vertebrae of the spinal column for the treatment of various spinal conditions. Fasteners can be provided to secure the implant to a particular location along the spinal column. The implants can be provided to stabilize the spinal column for treatment, either by fixing the spinal column or by permitting at least some motion of the stabilized motion segments.

Multi-axial and uni-axial screws have been employed for securing elongated implants, such as rods, along one or more motion segments of the spinal column. Bolts, screws, and hooks are typically secured to the vertebrae for connection to the supporting rod. These vertebral anchors must frequently be positioned at various angles due to the anatomical structure of the patient, the physiological problem being treated, and the preference of the physician. It is difficult to secure connections between the spinal support rod and the vertebral anchors at all the various angles and elevations that are required, especially where there are different distances between the rod and bolts and where these components are located at different heights on the patient.

In the field of orthopedic stabilization and specifically, spinal fixation of vertebrae, there exist numerous devices designed to allow the surgeon to place screws, helical spikes, pegs, or other bone attachment means within bone tissue, and are adapted to allow the attachment of rods, plates, or other longitudinal support members in order to stabilize one vertebrae to adjacent vertebrae, and thereby, assist in the fusion or healing process of adjacent vertebrae. As mentioned earlier, these devices may be mono-axial which require a 90-degree connection between the axis of the screw and the axis of the rod, or can be poly-axial or variable-angle, thus allowing a rod/screw connection of an angle other than perpendicular. Examples of the aforementioned can be found in U.S. Pat. Nos. 6,280,442 and 5,474,555. Further, there exist some devices that allow both poly-axial positioning as well as variable dorsal height positioning (see U.S. Pat. Nos. 6,626,906 and 5,885,285). There have existed bone screws that contain a bulbous or cylindrical body portion that engage the bone opening and help secure the attachment of the bone screw to the bone (see U.S. Pat. No. 4,854,311).

However, there is a need for a connection assembly between a spinal rod and a vertebral anchor that allows the surgeon to fix the desired elevation between the rod and the bone anchor as well as fix the desired angle between the anchor and the spinal rod. This need also encompasses the need for minimizing the profile and bulk of any of the components used to engage the bone screw to the spinal rod in a variety of angular orientations.

SUMMARY OF EXEMPLARY EMBODIMENTS OF THE INVENTION

The present invention is an orthopedic stabilization system of implants that includes a bulbous screw/bone interface, poly-axial fixation to the spinal rod, and variable height (dorsal in the case of posterior spinal pedicle fixation) positioning of the screw relative to the spinal rod.

In one aspect of the invention, the stabilization system attaches a spinal rod to vertebrae utilizing a bone attachment means, a post means, a locking means and a connector means. The bone attachment means includes a spherical cup member that forms one end, and an integral bone interface member at the other end that attaches directly to the vertebrae. The post means includes a spherical ball member at one end that interfaces to the spherical cup member forming a ball-joint arrangement, and a post member integral to the spherical ball member and forming the other end of the post means. This allows multi-angle positioning of the stabilization system. The locking means locks the bone attachment means to the post means in a determined spatial orientation as formed in the ball-joint arrangement, thus assisting with poly-axial fixation. The connector means attaches the spinal rod to the post member at a determined height, thus providing variable height adjustment.

In another aspect of the invention, the aforementioned stabilization system includes the use of shape memory alloy (SMA). The austenitic transformation of SMA alloy material due to temperature variants can effect the locking of either the ball-joint arrangement, the post means to the spinal rod, or both.

In yet another aspect of the invention, the aforementioned stabilization system includes embodiments wherein the ball-joint arrangement components are made of either metal or polymer and locked by the use of ultrasonic welding or using adhesives between the structural surfaces.

In still yet another aspect of the invention, the aforementioned stabilization system utilizes mechanical locking means such as screw fasteners, taper-locking interfaces and collets.

Other exemplary embodiments of the invention will become apparent from the detailed description provided hereinafter. It should be understood that the detailed description and specific examples, while disclosing exemplary embodiments of the invention, are intended for purposes of illustration only and are not intended to limit the scope of the invention.

BRIEF DESCRIPTION OF THE DRAWINGS

Exemplary embodiments of the present invention will become more fully understood from the detailed description and the accompanying drawings, wherein:

FIG. 3A is a front view cut-away of a fourth embodiment of the present invention.

FIG. 3B is a front view of a fifth embodiment of the present invention.

FIG. 4A is a front view cut-away of a sixth embodiment of the present invention.

FIG. 4B is a front view of a seventh embodiment of the present invention.

FIG. 6A is a front view cut-away of a tenth embodiment of the present invention.

FIG. 6B is a partial cut-away front view of an eleventh embodiment of the present invention.

DETAILED DESCRIPTION OF EXEMPLARY EMBODIMENTS

Figure 1A:
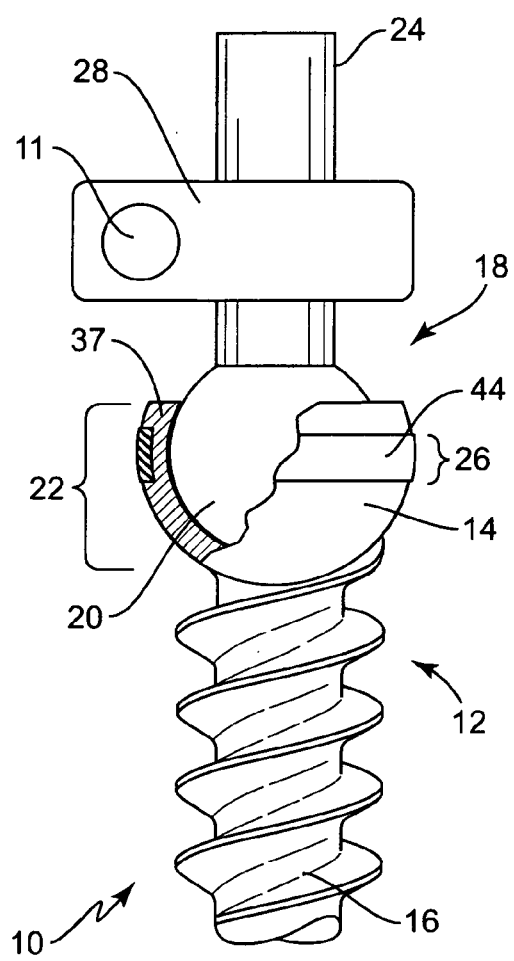
FIG. 1A is a front view cut-away of a first embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates. The following description of the embodiment(s) is merely exemplary (illustrative) in nature and is in no way intended to limit the invention, its application, or uses.

Figure 1B:
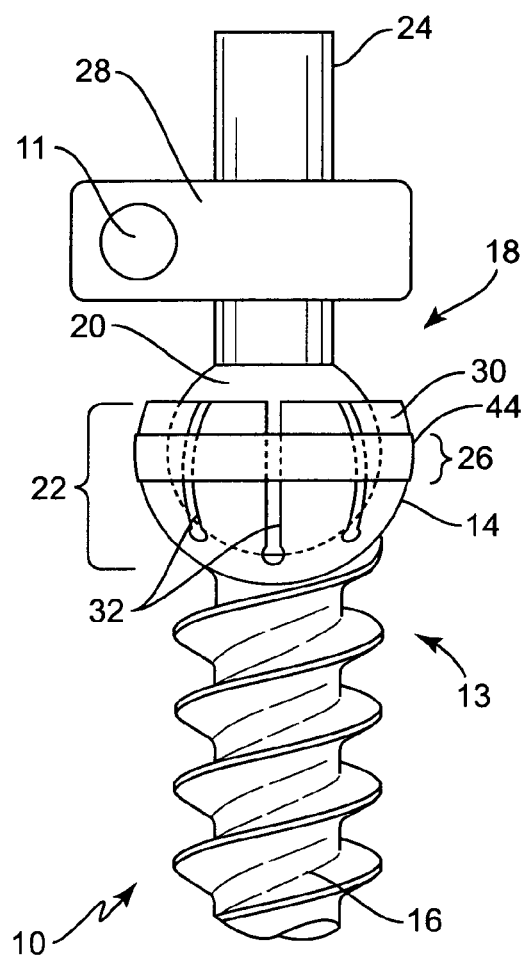
FIG. 1B is a front view of a second embodiment of the present invention.

FIGS. 1A and 1B describe first and second embodiments, respectively, of the present invention. In FIG. 1A, the orthopedic stabilization system 10 attaches a spinal rod 11 to vertebrae using a bone attachment means 12, a post means 18, a locking means 26 and a connector means 28. A spherical cup member 14 forms one end of the bone attachment means 12. A bone interface member 16, integral to the spherical cup member 14, forms the other end of the bone attachment means 12. The bone interface member 16 interfaces to the vertebrae directly. Not shown, are tangs or indentions on the external spherical portion of the spherical cup member 14 to be used together with a screwdriver of mating design for insertion of the bone attachment means 12 into the vertebrae. A spherical ball member 20 forms one end of the post means 18. The spherical ball member 20 is sized to mate and interface with the spherical cup member 14 to form a ball-joint arrangement 22. A post member 24, integral to the spherical ball member 20, forms the other end of the post means 18. The aforementioned ball-joint arrangement 22 allows poly-axial orientations of the bone attachment means 12 in association with the post means 18. It should be understood that the aforementioned ball-joint arrangement 22 design is illustrative in nature and may include other designs that incorporate a ball in association with structure to allow resultant poly-axial orientations. The locking means 26 locks the bone attachment means 12 to the post means 18 in the determined spatial orientation. A relatively thin-walled portion 37 of the spherical cup member 14 can be encircled with a shape memory alloy (SMA) ring 44 to assist with fixation. By instituting a temperature change to the SMA ring 44 the ensuing austenitic transformation compresses the thin-walled portion 37 to close and lock the ball joint arrangement 22 in a determined orientation. The connector means 28 attaches the spinal rod 11 to the post member 24 at a determined height. The connector means 28 thus provides a variable height adjustment of the spinal rod 11 to the post member 24. In FIG. 1B, the spherical cup member 14 includes a plurality of fingers 30 that define a plurality of slots 32. Upon activation of the SMA ring 44, its diameter is decreased which compresses the plurality of fingers 30 against spherical ball member 20 to effect locking of the ball-joint arrangement 22. A threaded bone screw 13 may be used to attach the post means 18 to the vertebrae. Also, the bone attachment means 12, the locking means 26, the connector means 28, and the post means 18 may comprise metals and/or polymers to effect their operation. And, locking of the aforementioned structures may be accomplished by the use of ultrasonic welding and adhesives (not shown) between structural surfaces.

Figure 2:
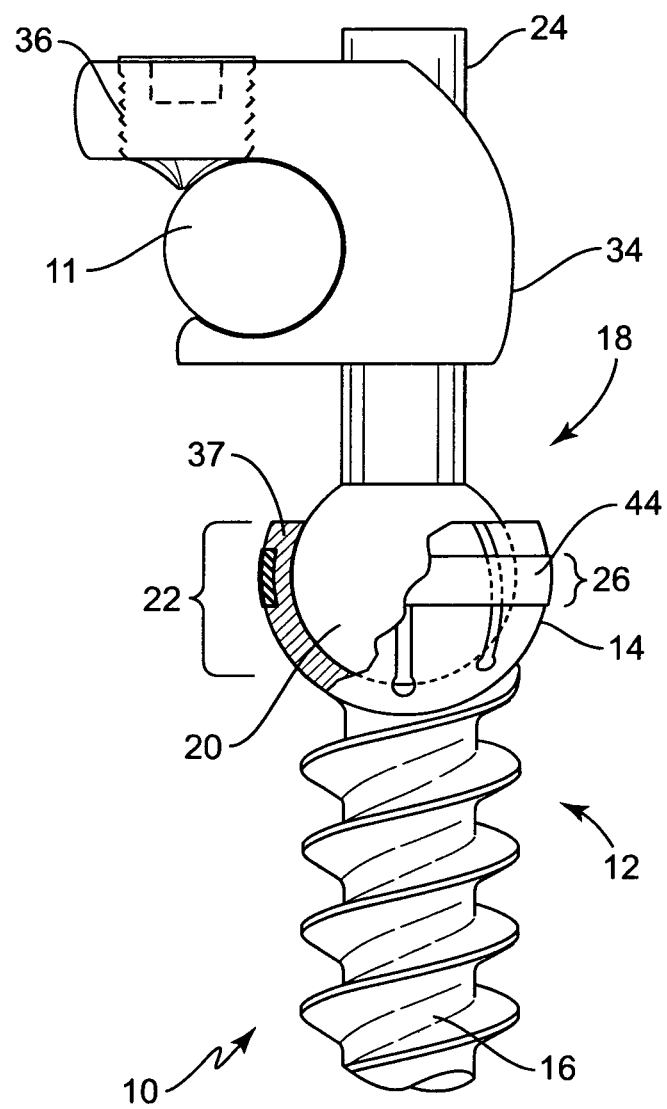
FIG. 2 is a front view of a third embodiment of the present invention.

FIG. 2 describes a third embodiment of the invention. In FIG. 2, a rod clamp means 34 attaches to a post member 24 at a determined height. The design structure of the rod clamp means 34 promotes variable height adjustment with the post member 24 as determined by the surgeon. A set screw locking mechanism 36 integral to the rod clamp means 34 rigidly locks the spinal rod 11 to the post means 18. The set screw locking mechanism 36 promotes mechanical interdigitation to rigidly connect to the spinal rod 11.

FIGS. 3A and 3B describe fourth and fifth embodiments, respectively, of the present orthopedic stabilization system 10. A collet locking mechanism 38 is used to rigidly connect the spinal rod 11 to the post means 18 (see FIG. 3A). The collet locking mechanism 38 is positioned on the post means 18 at a height determined by the surgeon. Here again, a locking means 26 may include an SMA ring 44 that compresses a plurality of fingers 30 to facilitate a fixation of a ball-joint arrangement 22 (see FIG. 3B). FIG. 3A also illustrates that the collet locking mechanism 38 may include a screw thread section 42. In practice, once the surgeon has inserted the spinal rod 11 into the rod clamp means 34, a post nut 40 is inserted onto the post means 18 and threaded onto the screw thread section 42. As the post nut 40 is tightened, both the spinal rod 11 and the collet locking mechanism 38 are squeezed into their desired relative positions. As mentioned above, the spherical cup member 14 may be modified to include a plurality of fingers 30 that define a plurality of slots 32 (see FIG. 3B). The remainder of the functional design is as described in FIG. 3A.

FIGS. 4A and 4B illustrate sixth and seventh embodiments, respectively, of the present invention. In FIG. 4A, the orthopedic stabilization system 10 incorporates a SMA connector 45 to act as a rod clamp means 34 and rigidly connect the spinal rod 11 to the post member 24. In practice, when a temperature differential is administered to the SMA connector 45, the austenitic transformation results in compression that locks the spinal rod 11 and the post member 24 in a desired relative position. Applying a temperature differential to a SMA ring 44 will compress a thin-walled portion 37 of the spherical cup member 14 and lock a spherical ball member 20 to the spherical cup member 14 in a determined spatial orientation. Similarly, the temperature differential, when administered to the SMA ring 44 will compress a plurality of fingers 30 (see FIG. 4B) in the spherical cup member 14 and promote a locking of a ball-joint arrangement 22 in a determined orientation.

Figure 5A:
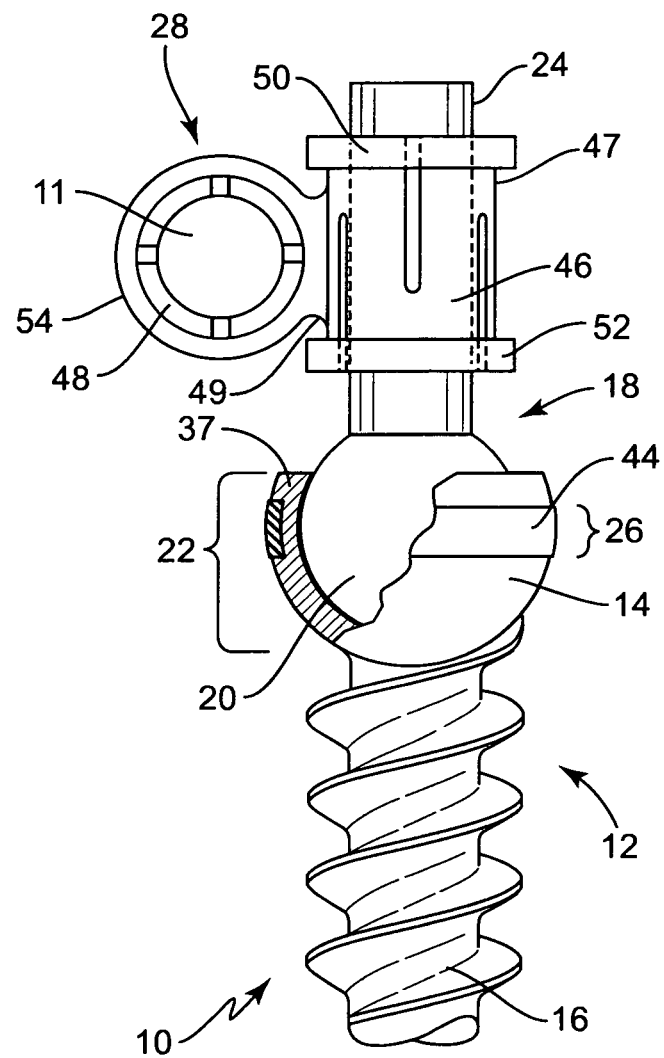
FIG. 5A is a front view cut-away of an eighth embodiment of the present invention.
Figure 5B:
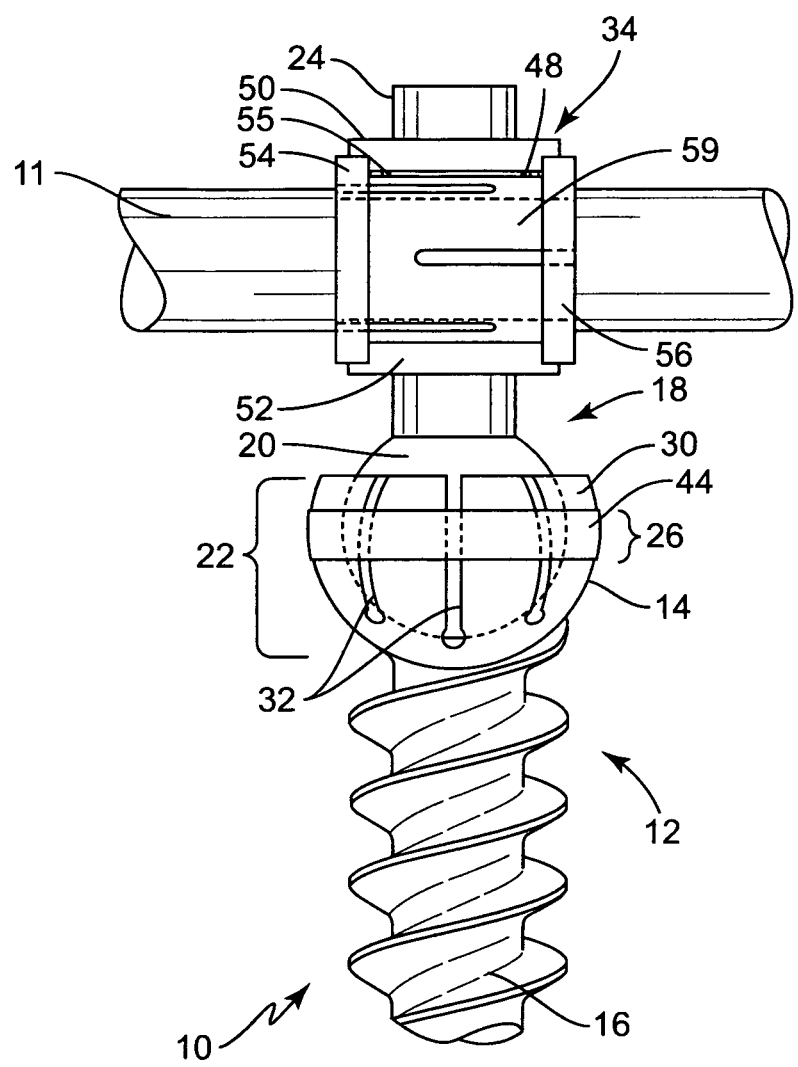
FIG. 5B is a front view of a ninth embodiment of the present invention.

FIGS. 5A and 5B describe eighth and ninth embodiments, respectively, of the present orthopedic stabilization system 10. In FIG. 5A, a spherical cup member 14 includes a thin-walled portion 37 that promotes compression when an encircling SMA ring 44 is activated. Compression of the SMA ring 44 locks a spherical ball member 20 to a spherical cup member 14 fixing a resultant ball-joint arrangement 22 in a determined spatial orientation. Two split collets are used to secure the spinal rod 11 to a post member 24. A first split collet 46 with a first SMA ring 50 at a first end 47 and a second SMA ring 52 at a second end 49 is positioned on a post member 24. A second split collet 48 with a third SMA ring 54 at a third end 55 and a fourth SMA ring 56 at a fourth end 59 is positioned on the spinal rod 11 (see FIG. 5B). The first split collet 46 is integral and positioned in a generally perpendicular spatial orientation to the second split collet 48. Upon activating the austenitic transformation of the SMA rings, the first and second split collets are tightened upon the post member 24 and the spinal rod 11 respectively, thereby forming a rigid connection between the spinal rod 11 and the post member 24, and the locked ball-joint-arrangement 22. In FIG. 5B, the spherical cup member 14 includes a plurality of fingers 30 that define a plurality of slots 32. The remainder of the functional design is as described in FIG. 5A.

FIGS. 6A and 6B describe tenth and eleventh embodiments, respectively, of the present orthopedic stabilization system 10. In FIG. 6A, the bone interface means 16 forms one end of the bone attachment means 12. A ball member 100, integral to the bone interface means 16, forms the other end of the bone attachment means 12. A cup member 102 forms one end of the post means 18. The cup member 102 is sized to mate and interface with the ball member 100 to form the ball-joint arrangement 22. The post member 24 is integral to the cup member 102 and forms the other end of the post means 18. As described in embodiments above, the locking means 26 locks the bone attachment means 12 to the post means 18 in a determined spatial orientation. A relatively thin-walled section 104 of the cup member 102 can be encircled with the SMA ring 44 to assist with fixation of the ball-joint arrangement 22. Any one of the connector means 28 described above in embodiments one through nine may be used to attach the spinal rod 11 to the post means 18. In FIG. 6B, the cup member 102 includes a plurality of cup fingers 106 that define a plurality of cup slots 108. The cup fingers 106 assist to effect locking of the ball-joint arrangement 22. In practice, the surgeon may use the design configurations described in FIGS. 6A and 6B in all of the embodiments described in FIGS. 1A through 5B.

Figure 7A:
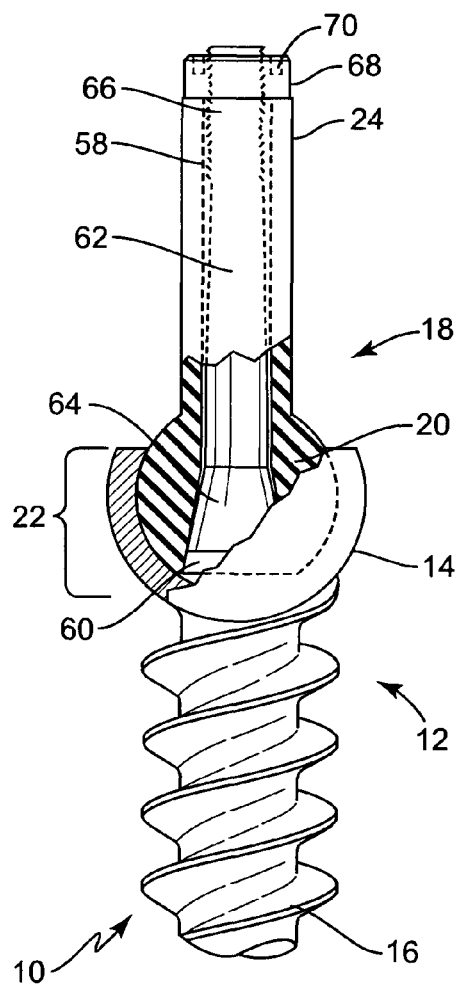
FIG. 7A is a front view cut-away of a twelfth embodiment of the present invention.
Figure 7B:
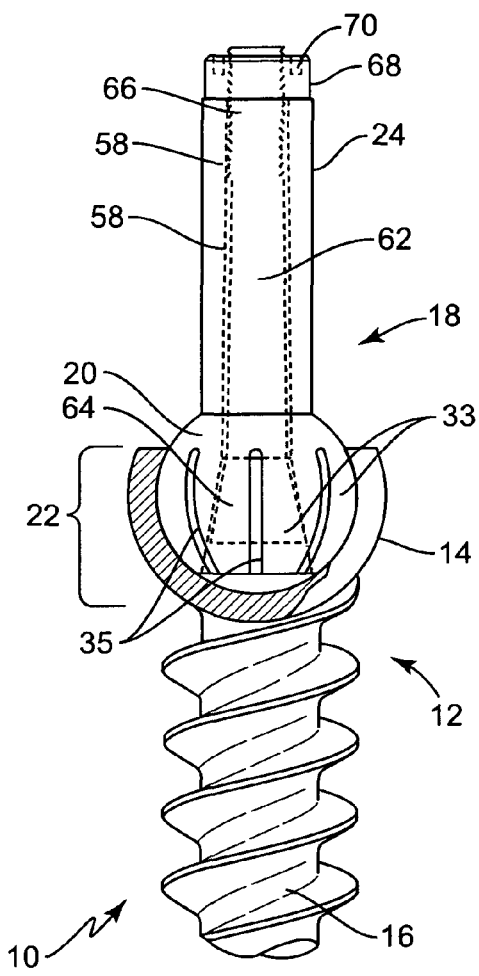
FIG. 7B is a partial cut-away front view of a thirteenth embodiment of the present invention.

FIGS. 7A and 7B describe twelfth and thirteenth embodiments, respectively, of the present orthopedic stabilization system 10. In FIG. 7A, a post means 18 includes a spherical ball member 20 that forms one end, and an integral post member 24 that forms the other end. The ball-joint arrangement 22 is formed by interfacing the spherical ball member 20 with a spherical cup member 14 of a bone attachment means 12. An interior 58 of the post means 18 defines an internal tapered slot 60. A tapered locking member 62 is positioned within the interior 58 of the post means 18 and mates structurally to the internal tapered slot 60. The tapered locking member 62 includes a mating tapered locking member 64 at the tapered end, and an integral threaded shaft 66 at the other end. The mating tapered locking member 64 is positioned within the spherical ball member 20. In assembly, the mating tapered locking member 64 is urged towards the bottom of the spherical ball member 20 at the tapered end leaving space such that the spherical ball member 20 can collapse in size sufficient to fit within the narrowed neck of the spherical cup member 14. After insertion within the spherical cup member 14, the spherical ball member 20 expands by spring force and rests within the interior 58 of the spherical cup member 14. In practice, when the surgeon is ready to lock the ball-joint arrangement 22, a nut 68, located proximally on the integral threaded shaft 66, is tightened against the upper surface (not shown) of the post member 24. The tightening of the tapered locking member nut 68 retracts the tapered locking member 62 and the mating tapered locking member 64 applies an outward wedging force against the interior 58 at the spherical cup member 14. A resultant expansion of the spherical ball member 20 locks the spherical ball member 20 to the spherical cup member 14, hence locking the ball-joint arrangement 22 in a determined spatial orientation. Tightening ports 70 may be located on the nut 68 to engage a mating tool (not shown) for tightening. The surgeon chooses any one of a connector means (not shown) such as those previously herein described to attach the spinal rod (not shown) to the post means 18. In FIG. 7B, the spherical ball member 20 includes a plurality of ball fingers 33 that define a plurality of ball slots 35. The spherically slotted spherical ball member 20 can expand in size in response to the tightening of the nut 68.

Figure 7C:
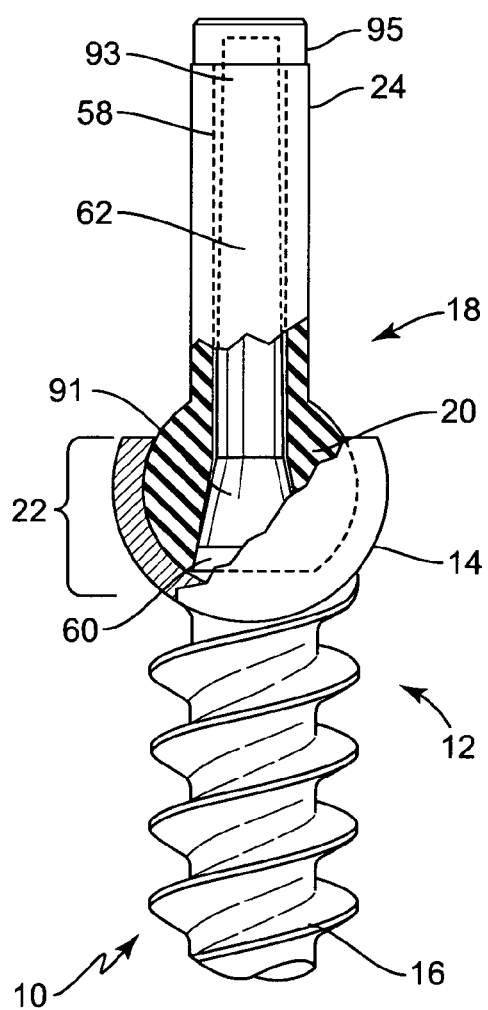
FIG. 7C is a front view cut-away of a fourteenth embodiment of the present invention.
Figure 7D:
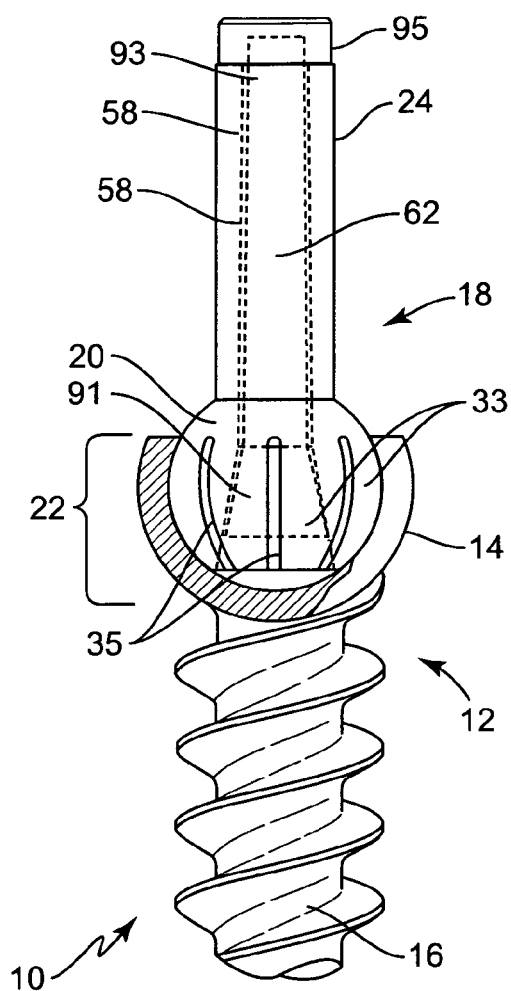
FIG. 7D is a partial cut-away front view of a fifteenth embodiment of the present invention.

FIGS. 7C and 7D describe fourteenth and fifteenth embodiments, respectively, of the present orthopedic stabilization system 10. These embodiments are similar in design to the twelfth and thirteenth embodiments with a few modifications. In FIGS. 7C and 7D, the tapered locking member 62 described above in FIGS. 7A and 7B includes a mating tapered SMA locking member 91 at the tapered end, and an integral SMA shaft 93 at the other end. A terminal end 95 is located on the SMA shaft 93 and forms the termination of the tapered locking member 62. In practice, when the surgeon is ready to lock the ball-joint arrangement 22, heat or other energy such as is commonly used in the operating room for electrocautery of tissue, is applied to the cap 95 or directly to the integral SMA shaft 93 or the mating SMA locking member 91 to activate the austenitic transformation of the SMA. Upon activation, the effective length of the tapered locking member 62 is shortened causing the tapered end to retract, thus applying an outward wedging force against the ball member 20. The resultant expansion locks the ball-joint arrangement 22 into a desired relative spatial orientation. The tapered locking member 62, which is comprised of both the mating tapered SMA locking member 91 and the integral SMA shaft 93, may be completely fabricated from SMA material, or alternatively, may be partially fabricated from SMA, with the remainder a suitable compatible material such as stainless steel, titanium, or chrome-cobalt alloy. The design is tailored to include the correct relative SMA to provide the proper degree of linear retraction necessary to effectively lock the ball-joint arrangement 22. In FIG. 7D, the spherical ball member 20 includes a plurality of ball fingers 33 that define a plurality of ball slots 35. The spherically slotted spherical ball member 20 can expand in size in response to the administration of heat or other energy to the mating tapered SMA locking member 91, the integral SMA shaft 93, or the cap 95.

Figure 8A:
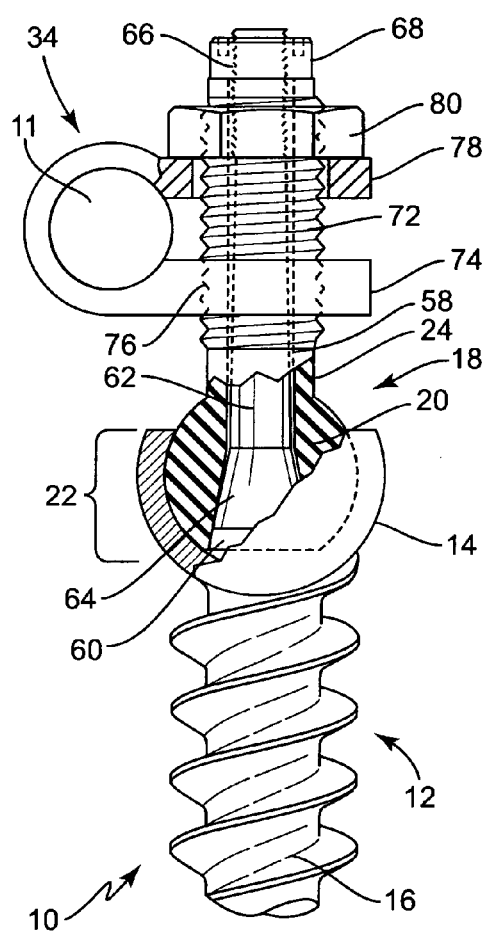
FIG. 8A is a front view cut-away of a sixteenth embodiment of the present invention.
Figure 8B:
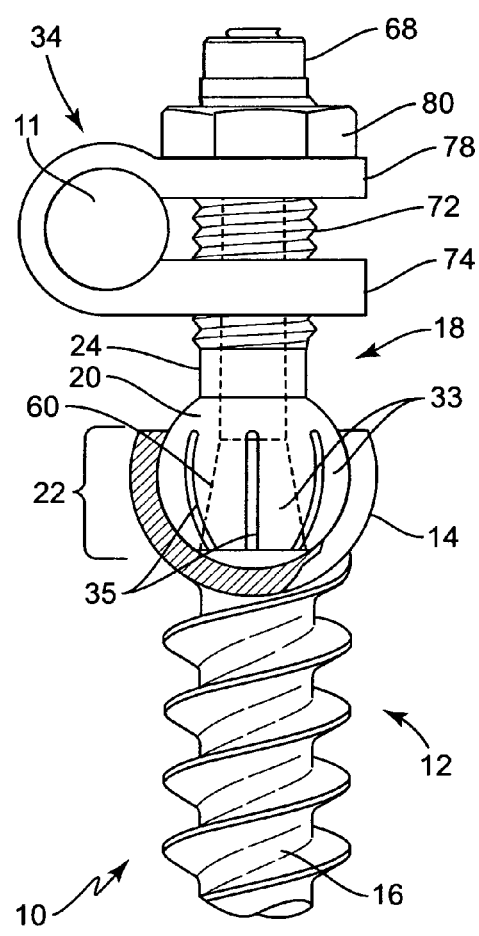
FIG. 8B is a partial cut-away view of a seventeenth embodiment of the present invention.

FIGS. 8A and 8B describe sixteenth and seventeenth embodiments, respectively, of the present orthopedic stabilization system 10. In FIG. 8A, a post member 24 includes a plurality of male threads 72 along a majority of its length. Threaded post members are useful for either spondylolisthesis reduction or any other deformity correction where gradual reduction of a bone screw and spine to which it may be attached, to the spinal rod is desired. A rod clamp means 34 is used that includes a lower part 74 that defines a first post slot (not shown) with female threads 76 that mate to the male threads 72 of the post member 24. The rod clamp means 34 also includes an upper part 78 that defines a second post slot (not shown) with a diameter larger than the major diameter of the male threads 72 of the post member 24. The aforementioned structural arrangement of the rod clamp means 34 promotes the lower part 74 of the rod clamp means 34 to thread onto the male threads 72 of the post member 24, while the upper part 78 passes freely over the male threads 72. A post clamp nut 80 is positioned on the male threads 72 of the post member 24, juxtaposed to the upper part 78, whereby upon tightening of the post clamp nut 80 rigidly locks together the spinal rod 11 and the rod clamp means 34. In practice, when the surgeon is ready to effect a reduction, torque is applied to the threaded post member 24, causing the rod clamp means 34 to move vertically along the post member 24. A tapered locking member 62, (as previously described in FIG. 7A), is snugly maintained such that a ball-joint arrangement 22 cannot collapse and dislodge from the spherical cup member 14 while reduction forces are applied. At such time that reduction is complete and the surgeon is ready to completely lock the stabilization system, a tapered locking member nut 68 is tightened to secure the ball-joint arrangement 22, and the post clamp nut 80 is tightened to lock the spinal rod 11. Alternatively, (not shown), the rod clamp means 34 may use both first and second slots with diameters larger than the male threads 72 of the post member 24. In this case, a lower nut would be required to pinch the spinal rod 11, or an alternative means may be used to secure the spinal rod 11. In FIG. 8B, the spherical ball member 20 includes a plurality of ball fingers 33 that define a plurality of ball slots 35 to assist in the locking of the ball-joint arrangement 22.

For purpose of clarity, some of the referenced figures describe a spherical cup member. In practice, any number of geometric configurations suitable to receive a ball, such as a conical V-shaped (not shown) or stair-stepped recess (not shown) could constitute a ball-joint arrangement as described. Also, the surface of any of the ball, cup, post, or internal surface of any connector may be textured, grooved, coated, or otherwise modified with mechanical interdigitation to enhance the locking strength of the connection.

Hence, the above description of embodiments of the invention is merely exemplary in nature and, thus, variations thereof are not to be regarded as a departure from the spirit and scope of the invention.

What is claimed is:

1. An orthopedic stabilization system to attach a spinal rod to vertebrae, comprising:
   a bone attachment means, including: a spherical cup member forming one end of said bone attachment means; and
   a bone interface member that is integral to said spherical cup member and forms the other end of said bone attachment means, and attaches to the vertebrae;
   a post means including a spherical ball member forming one end of said post means, and interfaces with said spherical cup member to form a ball joint arrangement; and
   a post member forming the other end of said post means, the post having a post height;
   wherein:
   said spherical ball member includes a plurality of ball fingers that define a plurality of ball slots;
   and an interior of said post means defines an internal tapered slot;
   a tapered locking member positioned within the interior of said post means and mating structurally to said internal tapered slot;
   wherein, said tapered locking member includes a mating tapered locking member at the tapered end and an integral threaded shaft at the other end, and with said mating tapered locking member positioned within said spherical ball member;
   a nut positioned proximally on said integral threaded shaft, external and juxtaposed to said post means; and
   a connector means to attach the spinal rod to said post member, the connector means having a connector height less than the post height such that the connector means can be positioned in a plurality of positions along the post height to provide a variable height adjustment between the spinal rod and bone attachment means.

2. The system of claim 1, wherein said nut includes at least one tightening port.

3. An orthopedic stabilization system to attach a spinal rod to vertebrae, comprising:
   a bone attachment means, including:
   a spherical cup member forming one end of said bone attachment means; and
   a bone interface member that is integral to said spherical cup member and forms the other end of said bone attachment means, and attaches to the vertebrae;
   a post means including a spherical ball member forming one end of said post means, and interfaces with said spherical cup member to form a ball-joint arrangement; and a post member at the other end of said post means;
   wherein:
   said spherical ball member includes a plurality of ball fingers that define a plurality of ball slots;
   said post member includes male threads along a majority of its length; and
   an interior of said post means defines an internal tapered slot;
   a tapered locking member positioned within the interior of said post means and mating structurally to said internal tapered slot;
   wherein, said tapered locking member includes a mating tapered locking member at the tapered end and an integral threaded shaft at the other end, whereby, said mating tapered locking member is positioned within said spherical ball member;
   a nut positioned proximally on said integral threaded shaft, external and juxtaposed to said post means, and whereupon tightening said nut, retracts said tapered end, applying an outward wedging force against said internal tapered slot; and a rod clamp means, comprising:
   a lower part defining a first post slot with female threads that mate to said male threads of said post member;
   an upper part defining a second post slot with a diameter larger than the major diameter of said male threads of said post member; and
   a post clamp nut positioned on said male threads of said post member and juxtaposed to said upper part, whereby, upon tightening, locks the spinal rod within said rod clamp means.

4. An orthopedic stabilization system to attach a spine rod to vertebrae, comprising:
   a bone screw having a screw thread on a bone attachment portion and a partially spherical cup on an opposing end portion;

a post member having a ball member on one end and a post extending from the ball member, the post having a post height and the ball member positioned in the partially spherical cup;

a locking member connected to said post member, the locking member moveable from an unlocked position allowing movement between the ball member and the partially spherical cup, and a locked position maintaining the ball member in a fixed position within the partially spherical cup; and a rod connector for attaching the spine rod to the post, the rod connector having a post engaging portion defining an aperture sized to receive the post, the post engaging portion having a height less than the post height such that the post engaging portion can be positioned in a plurality of locations along the post height to vary the distance between the rod and the bone screw;

wherein the post includes an interior passage with a tapered surface adjacent the ball member and the locking member includes an enlarged end configured to engage the tapered surface.

5. The system of claim 4, wherein the post has an outer diameter that is substantially constant between the ball member and an opposite end.

6. The system of claim 4, wherein the enlarged end transitions from a smaller dimension to a larger dimension adjacent the end of the locking member.

7. The system of claim 4, wherein the locking member comprises a shape memory alloy.

* * * * *